United States Patent
Siegert et al.

(10) Patent No.: US 7,713,387 B2
(45) Date of Patent: May 11, 2010

(54) METHOD FOR SEPARATING TRIOXANE FROM A TRIOXANE/FORMALDEHYDE/WATER MIXTURE BY MEANS OF PRESSURE CHANGE RECTIFICATION

(75) Inventors: Markus Siegert, Heidelberg (DE); Neven Lang, Mannheim (DE); Eckhard Ströfer, Mannheim (DE); Achim Stammer, Freinsheim (DE); Thorsten Friese, Mannheim (DE); Hans Hasse, Kaiserslautern (DE)

(73) Assignee: BASF Aktiengesellschaft (DE)

( * ) Notice: Subject to any disclaimer, the term of this patent is extended or adjusted under 35 U.S.C. 154(b) by 995 days.

(21) Appl. No.: 10/583,698

(22) PCT Filed: Dec. 21, 2004

(86) PCT No.: PCT/EP2004/014535
§ 371 (c)(1),
(2), (4) Date: Jun. 20, 2006

(87) PCT Pub. No.: WO2005/063733

PCT Pub. Date: Jul. 14, 2005

(65) Prior Publication Data
US 2007/0272540 A1 Nov. 29, 2007

(30) Foreign Application Priority Data
Dec. 23, 2003 (DE) ................. 103 61 516

(51) Int. Cl.
*B01D 3/00* (2006.01)
*C07D 323/06* (2006.01)
*C07C 45/78* (2006.01)

(52) U.S. Cl. ............................. 203/74; 203/14; 203/17; 203/75; 203/77; 203/78; 203/80; 549/368; 568/449; 159/47.1

(58) Field of Classification Search ................... 203/14, 203/17, 29, 73–75, 77–78, 80; 549/368; 568/448, 449; 159/47.1
See application file for complete search history.

(56) References Cited

U.S. PATENT DOCUMENTS 2,471,134 A 5/1949 Wright (Continued)

FOREIGN PATENT DOCUMENTS

DE 15 43 340 9/1969

(Continued)

*Primary Examiner*—Virginia Manoharan
(74) *Attorney, Agent, or Firm*—Collolly, Bove, Lodge & Hutz

(57) ABSTRACT

A process for removing trioxane from a use stream I of formaldehyde, trioxane and water, by
a) providing a use stream I of formaldehyde as the main component and trioxane and water as the secondary components,
b) mixing the use stream I with a recycle stream VII to obtain a feed stream Ia,
c) distilling the use stream Ia in a first distillation stage to obtain a stream II of formaldehyde as the main component and water as the secondary component, and a stream III of trioxane as the main component and water and formaldehyde as the secondary components,
d) distilling the stream III in a second distillation stage having a pressure higher than in the first distillation stage, to obtain a stream IV of trioxane and a stream V of trioxane as the main component and water and formaldehyde as the secondary components,
e) distilling the stream V in a third distillation stage to obtain a stream VI of water and the recycle stream VII of trioxane as the main component and water and formaldehyde as the secondary components.

29 Claims, 1 Drawing Sheet

U.S. PATENT DOCUMENTS

| | | | |
|---|---|---|---|
| 4,043,873 A * | 8/1977 | Ackermann et al. ............ 203/46 |
| 4,110,298 A | 8/1978 | Wells, III et al. |
| 4,230,533 A | 10/1980 | Giroux |
| 4,332,644 A | 6/1982 | Hamanaka et al. |
| 5,061,349 A * | 10/1991 | Kuppenbender et al. ...... 203/14 |
| 5,523,419 A | 6/1996 | Arnold |
| 5,766,424 A * | 6/1998 | Arnold et al. .................. 203/74 |
| 6,200,429 B1 | 3/2001 | Freyhof et al. |
| 6,201,136 B1 | 3/2001 | Reichl et al. |
| 6,610,888 B1 | 8/2003 | Ströfer et al. |
| 2005/0176973 A1 | 8/2005 | Friese et al. |
| 2006/0058537 A1* | 3/2006 | Haubs et al. ................. 549/368 |
| 2007/0155972 A1* | 7/2007 | Lang et al. ................... 549/326 |
| 2007/0260094 A1* | 11/2007 | Schelling et al. ............. 568/600 |
| 2008/0194845 A1* | 8/2008 | Lang et al. ................... 549/368 |
| 2008/0207954 A1* | 8/2008 | Stroefer et al. ............... 568/600 |
| 2008/0221368 A1* | 9/2008 | Stroefer et al. ............... 568/618 |
| 2008/0234459 A1* | 9/2008 | Lang et al. ................... 528/249 |
| 2008/0281109 A1* | 11/2008 | Lang et al. ................... 549/368 |
| 2009/0187033 A1* | 7/2009 | Siegert et al. ................ 549/368 |

FOREIGN PATENT DOCUMENTS

| | | |
|---|---|---|
| DE | 1 668 867 | 12/1971 |
| DE | 36 21 722 | 1/1988 |
| DE | 197 32 291 | 1/1999 |
| DE | 199 25 870 | 12/2000 |
| EP | 0 122 367 | 10/1984 |
| EP | 0 126 288 | 11/1984 |
| EP | 0 133 510 | 2/1985 |
| EP | 0 583 907 | 2/1994 |
| EP | 0 692 481 | 1/1996 |
| GB | 1172557 | 12/1969 |
| WO | WO-99/05137 | 2/1999 |
| WO | WO-03/097630 | 11/2003 |

* cited by examiner

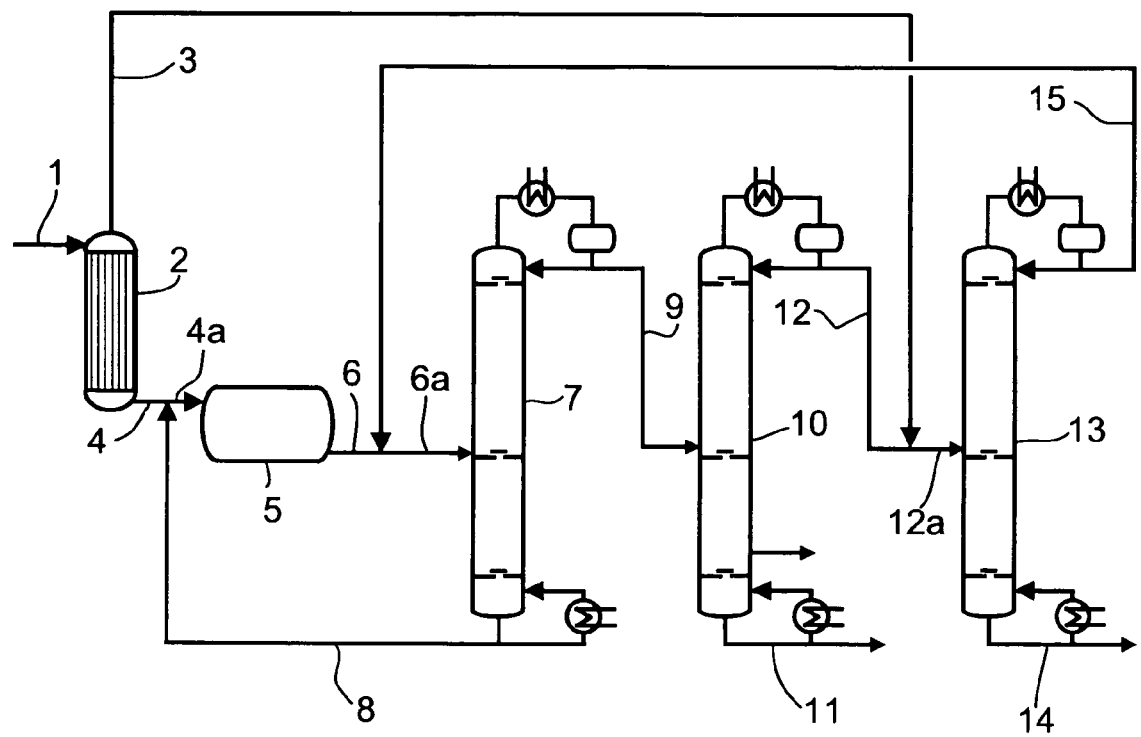

METHOD FOR SEPARATING TRIOXANE FROM A TRIOXANE/FORMALDEHYDE/WATER MIXTURE BY MEANS OF PRESSURE CHANGE RECTIFICATION

RELATED APPLICATIONS

This application is a national stage application (under 35 U.S.C. 371) of PCT/EP2004/014535 filed Dec. 21, 2004, which claims benefit to German application 103 61 516.4 filed Dec. 23, 2003.

The invention relates to a process for removing trioxane from a trioxane/formaldehyde/water mixture, and also to a process for preparing trixane.

Trioxane is generally prepared by distilling aqueous formaldehyde solution in the presence of acidic catalysts. The trioxane is subsequently removed from the distillate comprising formaldehyde and water by extraction with halogenated hydrocarbons such as methylene chloride or 1,2-dichloroethane, or other, water-immiscible solvents.

DE-A 1 668 867 describes a process for removing trioxane from mixtures comprising water, formaldehyde and trioxane by extraction with an organic solvent. In this process, an extraction section consisting of two subsections is charged at one end with a customary organic, virtually water-immiscible extractant for trioxane, and at the other end with water. Between the two subsections, the distillate of the trioxane synthesis to be separated is fed. On the side of the solvent feed, an aqueous formaldehyde solution is then obtained, and on the side of the water feed, a virtually formaldehyde-free solution of trioxane in the solvent. In one example, the distillate which is obtained in the trioxane synthesis and is composed of 40% by weight of water, 35% by weight of trioxane and 25% by weight of formaldehyde is metered into the middle section of a pulsation column, and methylene chloride is fed at the upper end of the column and water at the lower end of the column. In this case, an about 25% by weight solution of trioxane in methylene chloride is obtained at the lower end of the column and an about 30% by weight aqueous formaldehyde solution at the upper end of the column.

A disadvantage of this procedure is the occurrence of extractant which has to be purified. Some of the extractants used are hazardous substances (T or $T^+$ substances in the context of the German Hazardous Substances Directive), whose handling entails special precautions.

DE-A 197 32 291 describes a process for removing trioxane from an aqueous mixture which consists substantially of trioxane, water and formaldehyde, by removing trioxane from the mixture by pervaporation and separating the trioxane-enriched permeate by rectification into trioxane and an azeotropic mixture of trioxane, water and formaldehyde. In the example, an aqueous mixture consisting of 40% by weight of trioxane, 40% by weight of water and 20% by weight of formaldehyde is separated in a first distillation column under atmospheric pressure into a water/formaldehyde mixture and into an azeotropic trioxane/water/formaldehyde mixture. The azeotropic mixture is passed into a pervaporation unit which contains a membrane composed of polydimethylsiloxane with a hydrophobic zeolite. The trioxane-enriched mixture is separated in a second distillation column under atmospheric pressure into trioxane and, in turn, into an azeotropic mixture of trioxane, water and formaldehyde. This azeotropic mixture is recycled before the pervaporation stage.

A disadvantage of this procedure is the very high capital costs for the pervaporation unit.

It is an object of the invention to provide a process for removing trioxane from azeotropic trioxane/formaldehyde/water mixtures, which does not need any of the extraction steps or pervaporation steps of the prior art.

This object is achieved by a process for removing trioxane from a use stream I of formaldehyde, trioxane and water, by a) providing a use stream I which comprises formaldehyde as the main component and trioxane and water as the secondary components, b) mixing the use stream I with a recycle stream VII which comprises trioxane as the main component and formaldehyde and water as the secondary components to obtain a feed stream Ia which comprises formaldehyde as the main component and trioxane and water as the secondary components, c) distilling the use stream Ia in a first distillation stage at a pressure of from 0.1 to 2.5 bar to obtain a stream II which comprises formaldehyde as the main component and water as the secondary component, and a stream III which comprises trioxane as the main component and water and formaldehyde as the secondary components, d) distilling the stream III, optionally after removing low boilers from the stream III in a low boiler removal stage, in a second distillation stage at a pressure of from 0.2 to 17.5 bar, the pressure in the second distillation stage being from 0.1 to 15 bar higher than the pressure in the first distillation stage, to obtain a stream IV which consists substantially of trioxane and a stream V which comprises trioxane as the main component and water and formaldehyde as the secondary components, e) optionally mixing the stream V with a stream IX which comprises water as the main component to obtain a stream Va having a higher water content than the stream V, the stream Va comprising trioxane as the main component and water and formaldehyde as the secondary components, f) distilling the stream V or Va in a third distillation stage at a pressure of from 1 to 10 bar to obtain a stream VI which consists substantially of water and the recycle stream VII which comprises trioxane as the main component and water and formaldehyde as the secondary components.

The main component is the component having the larger or largest proportion by mass in the mixture in question. The proportion by mass of the particular component in the main mixture is preferably at least 50% by weight.

It is known that trioxane, formaldehyde and water form a ternary azeotrope which, at a pressure of 1 bar, has the composition of 69.5% by weight of trioxane, 5.4% by weight of formaldehyde and 25.1% by weight of water.

According to the invention, this azeotrope is circumvented by pressure swing distillation, in which a first and a second distillation are carried out at different pressures. In a first distillation column which is operated at lower pressure, the starting mixture Ia is separated into a trioxane/water mixture having low formaldehyde content III and a substantially trioxane-free formaldehyde/water mixture II. The formaldehyde/water mixture II may be recycled into the trioxane synthesis. In a further distillation column operated at higher pressure, the trioxane/formaldehyde/water mixture III obtained is separated into pure trioxane and a trioxane/formaldehyde/water mixture V having a lower trioxane content. According to the invention, the trioxane/formaldehyde/water mixture V (or Va) is also separated in a third distillation column into substantially pure water VI and a trioxane/formaldehyde/water mixture having a higher trioxane content VII. The latter is recycled upstream of the first distillation column. Preference is given to increasing the water content of the mixture V before the removal of water in the third distillation column by mixing in an aqueous stream IX.

Suitable distillation columns are any distillation columns such as packed or tray columns. These may contain any internals, structured packings or random packings.

The pressure in the second distillation stage is from 0.1 to 15 bar higher than the pressure in the first distillation stage. This pressure differential is preferably from 1.0 to 10 bar, more preferably from 1.5 to 5 bar.

All pressure data relate to the pressure at the top of the particular column.

The first distillation stage is carried out at a pressure of from 0.1 to 2.5 bar, preferably from 0.5 to 2.0 bar. The first distillation stage is generally carried out in a distillation column having at least 2, preferably from 2 to 50, more preferably from 4 to 25, theoretical plates. In general, the stripping section of this column includes at least 25%, preferably from 50 to 90%, of the theoretical plates of this column.

The feed stream Ia generally contains from 55 to 85% by weight of formaldehyde, from 15 to 35% by weight of water and from 3 to 20% by weight of trioxane. This stream Ia is separated into a stream II which is preferably drawn off at the top of the column, and a stream III which is preferably drawn off at the bottom of the column.

The stream II generally contains less than 1% by weight, preferably less than 0.1% by weight, of trioxane, more preferably less than 0.01% by weight of trioxane. For example, the composition of the stream II is as follows: from 65 to 85% by weight of formaldehyde, from 15 to 35% by weight of water and from 0 to 1% by weight of trioxane. The stream III generally contains more than 50% by weight, preferably more than 60% by weight, more preferably more than 70% by weight, of trioxane. For example, the composition of the stream III is as follows: from 3 to 20% by weight of formaldehyde, from 10 to 30% by weight of water and from 60 to 80% by weight of trioxane.

The stream II is preferably recycled into the trioxane synthesis.

The streams Ia, III, V, Va and VII may also contain up to 15% by weight of low boilers. Typical low boilers which can be formed in the trioxane synthesis and the subsequent distillative separation are methyl formate, methylal, dimethoxydimethyl ether, trimethoxydimethyl ether, methanol, formic acid, and also further hemiacetals and full acetals. To remove these low boilers, a low boiler removal stage may optionally be carried out between the first and the second distillation stage. In this case, the low boilers are preferably removed via the top of a low boiler removal column which is generally operated at a pressure of from 0.1 to 5 bar, preferably at a pressure of from 1.0 to 2.5 bar. In general, the low boiler removal column has at least 2 theoretical plates, preferably from 15 to 50 theoretical plates. The stripping section of this column generally includes from 25 to 90%, preferably from 50 to 75%, of the theoretical plates of this column. The content of the components having a lower boiling point than trioxane in the bottom effluent of the low boiler removal column is generally less than 5% by weight, preferably less than 2.5% by weight, more preferably less than 1.5% by weight.

In general, a low boiler removal is carried out.

The stream III is separated in a second distillation stage at a pressure of from 0.2 to 17.5 bar into a stream IV composed of substantially pure trioxane and a stream V which comprises trioxane, as the main component and additionally water and formaldehyde. This second distillation stage is preferably carried out at from 2.5 to 10 bar. In general, this second distillation stage is carried out in a distillation column having at least 2 theoretical plates, preferably from 10 to 50 theoretical plates, and the stream IV is obtained as a bottom draw stream or as a side draw stream in the stripping section of the column, and the stream V is obtained as a top draw stream. In general, the stripping section of the distillation column includes from 25 to 90%, preferably from 50 to 75%, of the theoretical plates of this column.

In general, the stream IV contains from 95 to 100% by weight, preferably from 99 to 100% by weight, of trioxane, and from 0 to 5% by weight, preferably from 0 to 1% by weight, of water and secondary components. Secondary components are in particular the abovementioned low boilers, but also components having a higher boiling point than trioxane. The content of water and secondary components in the trioxane stream IV is more preferably <0.1%. It may even be <0.01%. The stream V contains, for example, from 5 to 20% by weight of formaldehyde, from 15 to 35% by weight of water and from 50 to 75% by weight of trioxane.

In a preferred embodiment of the process according to the invention, before the third distillation step is carried out, an aqueous stream IX is mixed into the stream V to result in a stream Va which has a higher water content than the stream V. In general, the stream Va contains from 25 to 100% by weight of water. For example, the stream Va contains from 5 to 20% by weight of formaldehyde, from 25 to 45% by weight of water and from 40 to 65% by weight of trioxane.

The stream V or Va is separated in a third distillation stage at a pressure of from 1 to 10 bar into a stream VI which comprises substantially water and a recycle stream VII which comprises trioxane as the main component and additionally water and formaldehyde.

Preference is given to carrying out the third distillation stage at a pressure of from 2.5 to 5 bar. In general, the third distillation stage is carried out in a distillation column having at least two theoretical plates, preferably from 10 to 50 theoretical plates, and the water stream VI is obtained as a bottom draw stream or as a side draw stream in the stripping section of the column and the recycle stream VII as a top draw stream. The stripping section of this column generally includes from 25 to 95%, preferably from 70 to 90%, of the theoretical plates of this column.

A preferred distillation column for the third distillation stage is a dividing wall column, as described, for example, in U.S. Pat. Nos. 2,471,134, 4,230,533, EP-A 0 122 367, EP-A 0 126 288 and EP-A 0 133 510.

The water stream VI preferably consists of more than 95% by weight, more preferably of more than 99% by weight, of water. For example, the stream VI contains from 99 to 100% by weight of water and from 0 to 1% by weight of formaldehyde.

The stream VII contains, for example, from 5 to 40% by weight of formaldehyde, from 5 to 40% by weight of water and from 50 to 80% by weight of trioxane.

The stream VII may be partly or fully recycled upstream of the first distillation stage; preference is given to recycling it substantially fully upstream of the first distillation stage. It is mixed there with the use stream I.

The present invention also provides a process for preparing trioxane from an aqueous formaldehyde solution, by preparing the use stream I comprising formaldehyde, trioxane and water from an aqueous formaldehyde solution in a preceding trioxane synthesis stage and subsequently removing trioxane from the stream I as described above. Alternatively, the trioxane synthesis and the first distillation stage may be combined in a reactive distillation.

In one embodiment of the process according to the invention, a stream X composed of an aqueous formaldehyde solution of a preceding trioxane synthesis stage is fed and converted in the presence of acidic homogeneous or heterogeneous catalysts such as ion exchange resins, zeolites, sulfuric acid and p-toluenesulfonic acid at a temperature of generally from 70 to 130° C. Operation may be effected in a distillation column or an evaporator (reactive evaporator). The product mixture of trioxane/formaldehyde and water is then obtained as a vaporous vapor draw stream of the evaporator or as a top draw stream at the top of the column. The trioxane synthesis stage may also be carried out in a fixed bed or fluidized bed reactor over a heterogeneous catalyst, for example an ion exchange resin or zeolite.

In a further embodiment of the process according to the invention, the trioxane synthesis stage and the first distillation stage are carried out as a reactive distillation in one reaction column. This may contain a fixed catalyst bed of a heterogeneous acidic catalyst in the stripping section. Alternatively, the reactive distillation may also be carried out in the presence of a homogeneous catalyst, in which case the acidic catalyst is present in the column bottom together with the aqueous formaldehyde solution.

In general, the aqueous formaldehyde solution which is fed to the trioxane synthesis stage contains from 60 to 85% by weight of formaldehyde and from 15 to 40% by weight of water. This solution may be obtained in a preceding concentration step from an aqueous formaldehyde solution having low formaldehyde concentration. The concentration step may be carried out, for example, in an evaporator, preferably a falling-film evaporator.

The preceding concentration step may be carried out, for example, as described in DE-A 199 25 870.

In one embodiment of the process according to the invention, a stream XI of an aqueous formaldehyde solution is concentrated in an evaporator, preferably a falling-film evaporator, to obtain a stream X consisting of an aqueous formaldehyde solution having a higher formaldehyde concentration. The vapor draw stream of the evaporator which is highly depleted in formaldehyde is mixed as the aqueous stream IX with the stream V. Stream XI contains, for example, from 50 to 70% by weight of formaldehyde and from 30 to 50% by weight of water. Stream X contains, for example, from 65 to 80% by weight of formaldehyde and from 20 to 35% by weight of water. Stream IX contains, for example, from 10 to 25% by weight of formaldehyde and from 75 to 90% by weight of water.

The resulting pure trioxane, whose purity may be >99% by weight, >99.9% by weight or even >99.99% by weight, is preferably used to prepare polyoxymethylene (POM), polyoxymethylene derivatives such as polyoxymethylene dimethyl ether (POMDME) and diaminodiphenylmethane (MDA).

The invention is illustrated in detail hereinbelow with reference to the drawing.

FIG. 1 shows an example of an embodiment of the process according to the invention.

An aqueous formaldehyde solution 1 is fed to the evaporator 2, for example a thin-film evaporator, falling-film evaporator or helical-tube evaporator. The vapor draw stream 3 (stream IX) of the evaporator which is obtained is a formaldehyde-depleted aqueous solution, the bottom draw stream 4 (stream X) of the evaporator a formaldehyde-rich aqueous solution. The latter is combined with the formaldehyde-rich bottom draw stream 8 (stream II) of the first distillation column 7 to give the feed stream 4a (stream Xa). This is fed to the trioxane synthesis reactor 5 which is configured as an evaporator, stirred tank or fixed bed or fluidized bed reactor. The trioxane/formaldehyde/water mixture 6 (stream I) leaving the trioxane synthesis reactor is combined with the trioxane-rich top draw stream 15 (stream VII) of the third distillation column 13 to give the stream 6a (stream Ia). The stream 6a is fed to the first distillation column 7 and separated there into a formaldehyde/water stream 8 (stream II) and a formaldehyde/water/trioxane stream 9 (stream III). The stream 8 is obtained as a bottom draw stream and the stream 9 as a top draw stream. Stream 8 is combined with stream 4 and recycled into the reactor 5. Stream 8 is combined with stream 4 and recycled into the reactor 5. The formaldehyde/water/trioxane stream 9 is fed to the distillation column 10 and separated there into a bottom draw stream 11 (stream IV) composed substantially of pure trioxane and a top draw stream 12 (stream V) which comprises predominantly trioxane and additionally water and formaldehyde. The stream 12 is combined with the low-formaldehyde aqueous vapor draw stream 3 (stream IX) of the evaporator 2 to give the stream 12a (stream Va). The latter is fed to a third distillation column 13 and separated there into a stream 14 (stream VI) which consists substantially of water, and the recycle stream 15 (stream VII) which comprises predominantly trioxane and additionally water and formaldehyde.

EXAMPLE

In the theoretical simulation of the process illustrated in the figure, streams 6, 6a, 8, 9, 11, 12, 3, 12a, 14 and 15 of the compositions reported in the tables were obtained. The following parameters were selected: the first distillation stage is carried out at a pressure of 0.8 bar in a column 7 having 5 theoretical plates. The reflux ratio is 1.25, the top temperature 85° C. and the bottom temperature 97° C. The feed 6a is disposed at the height of the 3rd theoretical plate. The second distillation stage is carried out at a pressure of 4.0 bar in a column 10 having 17 theoretical plates. The reflux ratio is 0.1, the top temperature 131° C., and the bottom temperature 167° C. The feed 9 is disposed at the height of the 10th theoretical plate. The third distillation stage is carried out at a pressure of 2.5 bar in a column 13 having 25 theoretical plates. The reflux ratio is 1.5, the top temperature 114° C. and the bottom temperature 127° C. The feed 12a is disposed at the height of the 20th theoretical plate.

| | Stream | | | | | | | | | |
|---|---|---|---|---|---|---|---|---|---|---|
| | 6 (I) | 6a (Ia) | 8 (II) | 9 (III) | 11 (IV) | 12 (V) | 3 (IX) | 12a (Va) | 14 (VI) | 15 (VII) |
| Mass flow rate [kg/h] | 75.3 | 85.8 | 71.9 | 14.0 | 3.0 | 11.0 | 2.7 | 13.6 | 3.1 | 10.5 |
| Formaldehyde [% by wt.] | 70.5 | 64.1 | 74.5 | 10.5 | 0.0 | 13.4 | 15.0 | 13.7 | 0.07 | 17.8 |

-continued

|  | Stream | | | | | | | | | |
|---|---|---|---|---|---|---|---|---|---|---|
|  | 6 (I) | 6a (Ia) | 8 (II) | 9 (III) | 11 (IV) | 12 (V) | 3 (IX) | 12a (Va) | 14 (VI) | 15 (VII) |
| Water [% by wt.] | 25.5 | 24.4 | 25.5 | 19.1 | 0.001 | 24.3 | 85.0 | 36.1 | 99.92 | 17.2 |
| Trioxane [% by wt.] | 4.0 | 11.5 | 0.01 | 70.4 | 99.999 | 62.3 | 0.0 | 50.2 | 0.01 | 65.1 |

What is claimed is:

1. A process for removing trioxane from a use stream I of formaldehyde, trioxane and water, by
   a) providing a use stream I which comprises formaldehyde as the main component and trioxane and water as the secondary components,
   b) mixing the use stream I with a recycle stream VII which comprises trioxane as the main component and formaldehyde and water as the secondary components to obtain a feed stream Ia which comprises formaldehyde as the main component and trioxane and water as the secondary components,
   c) distilling the use stream Ia in a first distillation stage at a pressure of from 0.1 to 2.5 bar to obtain a stream II which comprises formaldehyde as the main component and water as the secondary component, and a stream III which comprises trioxane as the main component and water and formaldehyde as the secondary components,
   d) distilling the stream III, optionally after removing low boilers from the stream III in a low boiler removal stage, in a second distillation stage at a pressure of from 0.2 to 17.5 bar, the pressure in the second distillation stage being from 0.1 to 15 bar higher than the pressure in the first distillation stage, to obtain a stream IV which consists substantially of trioxane and a stream V which comprises trioxane as the main component and water and formaldehyde as the secondary components,
   e) optionally mixing the stream V with a stream IX which comprises water as the main component to obtain a stream Va having a higher water content than the stream V, the stream Va comprising trioxane as the main component and water and formaldehyde as the secondary components,
   f) distilling the stream V or Va in a third distillation stage at a pressure of from 1 to 10 bar to obtain a stream VI which consists substantially of water and the recycle stream VII which comprises trioxane as the main component and water and formaldehyde as the secondary components;
   wherein a low boiler removal stage is carried out between the first and the second distillation stage, in which low boilers selected from a group consisting of methyl formate, methylal, dimethoxydimethyl ether and methanol are removed from the stream III; and
   wherein the low boiler removal is carried out at a pressure of from 0.1 to 5.0 bar in a distillation column having at least 2 theoretical plates.

2. The process according to claim 1, wherein the pressure in the second distillation stage is from 1.0 to 10 bar higher than the pressure in the first distillation stage.

3. The process according to claim 1, wherein the first distillation stage is carried out at a pressure of from 0.75 to 1.25 bar.

4. The process according to claim 1, wherein the third distillation stage is carried out at a pressure of from 2.5 to 5 bar.

5. The process according to claim 1, wherein the first distillation stage is carried out in a first distillation column having at least two theoretical plates, the second distillation stage in a second distillation column having at least 2 theoretical plates and the third distillation stage in a third distillation column having at least two theoretical plates.

6. The process according to claim 5, wherein a stripping section of the first distillation column has from 60 to 90% of the number of theoretical plates of this column.

7. The process according to claim 5, wherein a stripping section of the second distillation column has from 50 to 75% of the number of theoretical plates of this column.

8. The process according to claim 5, wherein a stripping section of the third distillation column has from 70 to 90% of the number of theoretical plates of this column.

9. A process for preparing trioxane from an aqueous formaldehyde solution, by feeding a stream X of an aqueous formaldehyde to a trioxane synthesis stage and converting it under acidic conditions to obtain the stream I, and removing trioxane from the stream I by the process according to claim 1.

10. The process according to claim 9, wherein the stream X is obtained from a stream XI of an aqueous formaldehyde solution of low formaldehyde concentration by concentrating in an evaporator.

11. A process for removing trioxane from a use stream I of formaldehyde, trioxane and water, by
   a) providing a use stream I which comprises formaldehyde as the main component and trioxane and water as the secondary components,
   b) mixing the use stream I with a recycle stream VII which comprises trioxane as the main component and formaldehyde and water as the secondary components to obtain a feed stream Ia which comprises formaldehyde as the main component and trioxane and water as the secondary components,
   c) distilling the use stream Ia in a first distillation stage at a pressure of from 0.1 to 2.5 bar to obtain a stream II which comprises formaldehyde as the main component and water as the secondary component, and a stream III which comprises trioxane as the main component and water and formaldehyde as the secondary components,
   d) distilling the stream III, optionally after removing low boilers from the stream III in a low boiler removal stage, in a second distillation stage at a pressure of from 0.2 to 17.5 bar, the pressure in the second distillation stage being from 0.1 to 15 bar higher than the pressure in the first distillation stage, to obtain a stream IV which consists substantially of trioxane and a stream V which comprises trioxane as the main component and water and formaldehyde as the secondary components, e) optionally mixing the stream V with a stream IX which comprises water as the main component to obtain a stream Va having a higher water content than the stream V, the stream Va comprising trioxane as the main component and water and formaldehyde as the secondary components, f) distilling the stream V or Va in a third distillation stage at a pressure of from 1 to 10 bar to obtain a stream VI which consists substantially of water and the recycle stream VII which comprises trioxane as the main component and water and formaldehyde as the secondary components;

the following are the compositions of streams I-VII:

stream I: from 60 to 80% by weight of formaldehyde, from 15 to 35% by weight of water, from 1 to 15% by weight of trioxane;

stream Ia: from 55 to 75% by weight of formaldehyde, 15 to 35% by weight of water, 3 to 20% by weight of trioxane;

stream II: from 65 to 85% by weight of formaldehyde, 15 to 35% by weight of water, 0 to 1% by weight of trioxane;

stream III: from 3 to 20% by weight of formaldehyde, 10 to 30% by weight of water, 60 to 80% by weight of trioxane;

stream IV: from 95 to 100% by weight of trioxane, 0 to 5% by weight of water and secondary components;

stream V: from 5 to 20% by weight of formaldehyde, 15 to 35% by weight of water, 50 to 75% by weight of trioxane;

stream Va: from 5 to 20% by weight of formaldehyde, 25 to 45% by weight of water, 40 to 65% by weight of trioxane;

stream VI: from 0 to 1% by weight of formaldehyde, 99 to 100% by weight of water;

stream VII: from 5 to 30% by weight of formaldehyde, 5 to 30% by weight of water, 50 to 80% by weight of trioxane, and the streams I, Ia, III, V, Va and VII may also contain up to 15% by weight of low boilers selected from the group consisting of methyl formate, methylal, dimethoxydimethyl ether and methanol.

12. The process according to claim 11, wherein the pressure in the second distillation stage is from 1.0 to 10 bar higher than the pressure in the first distillation stage.

13. The process according to claim 11, wherein the first distillation stage is carried out at a pressure of from 0.75 to 1.25 bar.

14. The process according to claim 11, wherein the third distillation stage is carried out at a pressure of from 2.5 to 5 bar.

15. The process according to claim 11, wherein the first distillation stage is carried out in a first distillation column having at least two theoretical plates, the second distillation stage in a second distillation column having at least 2 theoretical plates and the third distillation stage in a third distillation column having at least two theoretical plates.

16. The process according to claim 15, wherein a stripping section of the first distillation column has from 60 to 90% of the number of theoretical plates of this column.

17. The process according to claim 15, wherein a stripping section of the second distillation column has from 50 to 75% of the number of theoretical plates of this column.

18. The process according to claim 15, wherein a stripping section of the third distillation column has from 70 to 90% of the number of theoretical plates of this column.

19. A process for preparing trioxane from an aqueous formaldehyde solution, by feeding a stream X of an aqueous formaldehyde to a trioxane synthesis stage and converting it under acidic conditions to obtain the stream I, and removing trioxane from the stream I by the process according to claim 11.

20. The process according to claim 19, wherein the stream X is obtained from a stream XI of an aqueous formaldehyde solution of low formaldehyde concentration by concentrating in an evaporator.

21. A process for removing trioxane from a use stream I of formaldehyde, trioxane and water, by a) providing a use stream I which comprises formaldehyde as the main component and trioxane and water as the secondary components, b) mixing the use stream I with a recycle stream VII which comprises trioxane as the main component and formaldehyde and water as the secondary components to obtain a feed stream Ia which comprises formaldehyde as the main component and trioxane and water as the secondary components, c) distilling the use stream Ia in a first distillation stage at a pressure of from 0.1 to 2.5 bar to obtain a stream II which comprises formaldehyde as the main component and water as the secondary component, and a stream III which comprises trioxane as the main component and water and formaldehyde as the secondary components, d) distilling the stream III, optionally after removing low boilers from the stream III in a low boiler removal stage, in a second distillation stage at a pressure of from 0.2 to 17.5 bar, the pressure in the second distillation stage being from 0.1 to 15 bar higher than the pressure in the first distillation stage, to obtain a stream IV which consists substantially of trioxane and a stream V which comprises trioxane as the main component and water and formaldehyde as the secondary components, e) optionally mixing the stream V with a stream IX which comprises water as the main component to obtain a stream Va having a higher water content than the stream V, the stream Va comprising trioxane as the main component and water and formaldehyde as the secondary components, f) distilling the stream V or Va in a third distillation stage at a pressure of from 1 to 10 bar to obtain a stream VI which consists substantially of water and the recycle stream VII which comprises trioxane as the main component and water and formaldehyde as the secondary components, feeding a stream X of an aqueous formaldehyde to a trioxane synthesis stage and converting it under acidic conditions to obtain the stream I, and removing trioxane from the stream I;

wherein the stream X is obtained from a stream XI of an aqueous formaldehyde solution of low formaldehyde concentration by concentrating in an evaporator; and wherein the stream IX is the formaldehyde-depleted vapor draw stream of the evaporator.

22. The use of trioxane, preparable by the process according to claim 21, for preparing polyoxymethylene (POM), polyoxymethylene derivatives and diaminodiphonylmethane (MDA).

23. The process according to claim 21, wherein the pressure in the second distillation stage is from 1.0 to 10 bar higher than the pressure in the first distillation stage.

24. The process according to claim 21, wherein the first distillation stage is carried out at a pressure of from 0.75 to 1.25 bar.

25. The process according to claim 21, wherein the third distillation stage is carried out at a pressure of from 2.5 to 5 bar.

26. The process according to claim 21, wherein the first distillation stage is carried out in a first distillation column having at least two theoretical plates, the second distillation stage in a second distillation column having at least 2 theoretical plates and the third distillation stage in a third distillation column having at least two theoretical plates.

27. The process according to claim 26, wherein a stripping section of the first distillation column has from 60 to 90% of the number of theoretical plates of this column.

28. The process according to claim 26, wherein a stripping section of the second distillation column has from 50 to 75% of the number of theoretical plates of this column.

29. The process according to claim 26, wherein a stripping section of the third distillation column has from 70 to 90% of the number of theoretical plates of this column.

* * * * *